United States Patent
Bokrantz et al.

(10) Patent No.: US 10,974,068 B2
(45) Date of Patent: Apr. 13, 2021

(54) METHOD, COMPUTER PROGRAM AND SYSTEM FOR OPTIMIZING A RADIOTHERAPY TREATMENT PLAN

(71) Applicant: RaySearch Laboratories AB, Stockholm (SE)

(72) Inventors: Rasmus Bokrantz, Stockholm (SE); Albin Fredriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 281 days.

(21) Appl. No.: 16/091,274

(22) PCT Filed: Apr. 5, 2017

(86) PCT No.: PCT/EP2017/058056
§ 371 (c)(1),
(2) Date: Oct. 4, 2018

(87) PCT Pub. No.: WO2017/174625
PCT Pub. Date: Oct. 12, 2017

(65) Prior Publication Data
US 2020/0324143 A1      Oct. 15, 2020

(30) Foreign Application Priority Data
Apr. 7, 2016   (EP) .................................. 16164234

(51) Int. Cl.
*A61N 5/10*          (2006.01)
(52) U.S. Cl.
CPC ......... *A61N 5/1038* (2013.01); *A61N 5/1031* (2013.01); *A61N 5/1037* (2013.01); *A61N 5/1039* (2013.01); *A61N 2005/1041* (2013.01)

(58) Field of Classification Search
CPC .. A61N 5/1031; A61N 5/1042; A61N 5/1037; A61N 5/103; A61N 5/1038;
(Continued)

(56) References Cited

U.S. PATENT DOCUMENTS

| 5,602,892 A | * | 2/1997 | Llacer | G16H 50/50 |
| | | | | 378/65 |
| 7,412,029 B2 | * | 8/2008 | Myles | A61N 5/1049 |
| | | | | 378/65 |

(Continued)

FOREIGN PATENT DOCUMENTS

| EP | 2 878 338 A1 | 6/2015 |
| WO | WO-2015/090457 A1 | 6/2015 |
| WO | WO-2015/090459 A1 | 6/2015 |

OTHER PUBLICATIONS

Fredriksson, A., et al., "Optimizing the Scenario Positions for Robust Radiation Therapy Treatment Planning," Oct. 10, 2012, Retrieved from URL:https://people.kth.se/~andersf/doc/scenariooptimization.pdf, 21 pages.

*Primary Examiner* — Irakli Kiknadze
(74) *Attorney, Agent, or Firm* — Faegre Drinker Biddle & Reath LLP

(57) ABSTRACT

A scenario-based treatment plan optimization method for radiotherapy treatment is proposed, in which a first and a second possible scenario are defined. Different optimization functions are defined for the scenarios and the treatment plan is optimized applying the first optimization function under the first scenario and the second optimization function under the second scenario, thereby obtaining a first optimized radiotherapy treatment plan.

11 Claims, 1 Drawing Sheet

(58) Field of Classification Search
CPC ............... A61N 5/1047; A61N 5/1067; A61N 2005/1061; A61N 5/1036; A61N 5/1049; A61N 2005/1041; A61N 5/10; A61N 2005/1035; A61N 5/1045; A61N 2005/1054; A61N 2005/1062; A61N 5/107; A61N 2005/1074; A61N 5/1039; A61N 5/1048; A61N 5/1077; A61N 2005/1087; A61N 2005/1095; A61N 2005/1096; A61N 5/1064; A61N 5/1071; A61N 2005/1032; A61N 2005/1034; A61N 5/1027; G06T 2207/10081; G06T 7/11; G06T 2207/30096; G06T 7/0012; G06T 2207/20092; G06T 2207/30004; G06T 2207/30008; G06T 7/13; G06T 7/174; G06T 2207/10072; G06N 20/00; G06N 7/005; A61B 6/032; A61B 6/04; A61B 6/0407; A61B 6/0487; A61B 6/40; A61B 6/4007; A61B 6/4014; A61B 6/52; A61B 6/5205; A61B 6/5211; A61B 6/5229; A61B 18/00; A61B 2034/101; A61B 34/10; A61B 5/0036; A61B 5/08; A61B 5/113; A61B 5/4836; H01L 2224/13147; H01L 2924/0002; H01L 2224/05552; H01L 2924/00014; H01L 21/6835; H01L 21/76898; H01L 2221/6835; H01L 2221/68368; H01L 2221/68377; H01L 2221/68381; H01L 2224/03002; H01L 2224/036; H01L 2224/03912; H01L 2224/0401; G16H 20/40; G16H 50/50
USPC ........................................................ 378/62, 65
See application file for complete search history.

(56) References Cited

U.S. PATENT DOCUMENTS

| | | | |
|---|---|---|---|
| 7,804,935 B2 * | 9/2010 | Yin | A61N 5/1031 378/65 |
| 8,767,917 B2 * | 7/2014 | Ruchala | G06F 19/3481 378/65 |
| 10,265,543 B2 * | 4/2019 | Bharat | A61B 18/00 |
| 2002/0051513 A1 * | 5/2002 | Pugachev | A61N 5/103 378/65 |
| 2005/0207531 A1 * | 9/2005 | Dempsey | A61N 5/1031 378/65 |
| 2010/0054411 A1 * | 3/2010 | Nord | A61N 5/1031 378/65 |

* cited by examiner

METHOD, COMPUTER PROGRAM AND SYSTEM FOR OPTIMIZING A RADIOTHERAPY TREATMENT PLAN

This application is the National Stage of International Application No. PCT/EP2017/058056, filed Apr. 5, 2017, and claims benefit of European Patent Application No. 16164234.3, filed Apr. 7, 2016, the entire contents of which are incorporated by reference herein.

TECHNICAL FIELD

The present invention relates to the optimization of a radiotherapy treatment plan and in particular a radiotherapy treatment plan that takes into account different scenarios.

BACKGROUND AND RELATED ART

Typically, radiotherapy treatment planning involves optimizing the plan to achieve one or more set goals. To try to achieve the goals as closely as possible, an optimization problem is defined. The optimization problem typically comprises an objective function having one or more objective function constituents, each relating to a goal that the optimization should strive towards. The optimization problem typically also comprises one or more constraints, that is, conditions that have to be fulfilled more strictly, such as a minimum dose to a tumour or a maximum dose to an organ at risk or bounds on the variables controlling the objective function.

When creating a radiotherapy treatment plan, there are usually some variables that cannot be known precisely. This means that there will always be some uncertainty. To account for such uncertainties, a number of different scenarios may be defined, each representing a possible set of variable values and the plan may be optimized to give a satisfactory result for all of the scenarios.

Uncertainties that can be accounted for include, but are not limited to:

Treatment preparation uncertainty. This may include, for example, uncertainty due to incorrect delineation, incorrect patient positioning during image acquisition, and inaccuracies in the conversion of CT-Hounsfield units to proton stopping powers.

Treatment execution uncertainty. These uncertainties may relate to variables within a treatment fraction, such as uncertainty in patient setup, organ movement and respiratory movement. Other treatment execution uncertainties are caused by changes over time, including tumour shrinkage, or general weight loss in the patient.

Parameter uncertainty, such as uncertainty in the estimation of radiobiological model parameters or in the dose prescription.

In scenario-based optimization methods, a number of scenarios are defined, each representing a possible configuration, or set of variables for one or more uncertainties. A set of goals is defined and a plan is optimized with the objective of meeting these goals as well as possible in all scenarios. Such optimization leads to plans that are less sensitive to error compared to an optimization conditioned only on a single scenario. The optimization may be performed, for example by trying to make the objective function for the worst case scenario meet certain minimum goals, or by minimizing a weighted average of the objective function over all scenarios.

The goals that are set may be related to minimum and maximum doses for targets and risk organs respectively, or to DVHs or another suitable measure of the treatment result. For example, a goal may be that at least a certain portion of the target should receive at least a certain minimum dose. In order to achieve a realizable plan the goals are set so that they can be met in all possible scenarios. It happens that one or more poor performance scenarios are only able to meet significantly lower goals than other scenarios. In such cases, the poor performance scenarios are typically ignored and the planning is performed only on the higher performance scenarios.

SUMMARY OF THE INVENTION

It is an aim of the present invention to further improve scenario-based methods for optimization of radiotherapy treatment plans.

The invention relates to a method for radiotherapy treatment plan optimization using a scenario-based optimization function to perform optimization based on at least a first and a second scenario, each scenario representing the realization of at least one uncertainty, the method comprising the steps of a. providing input data for treatment plan optimization;
b. defining a first optimization function for the first scenario;
c. defining a second optimization function for the second scenario, said second optimization function being different from the first optimization function;
d. optimizing a radiotherapy treatment plan applying the first optimization function under the first scenario and the second optimization function under the second scenario, thereby obtaining a first optimized radiotherapy treatment plan.

The first optimization function and/or the second optimization function may be included as a constraint in the optimization. Alternatively, the first optimization function and/or the second optimization function may be included as an objective function constituent in the optimization. It is also possible to include only one optimization function, or to include one optimization function as a constraint and the other as an objective function constituent. Typically goals are set for the treatment, and these goals are used to define objective function constituents, constraints or a combination of these. An objective function constituent is a desired goal, towards which the optimization should strive or which the optimization should try to fulfill as well as possible, whereas a constraint is a strict goal that must be satisfied precisely.

The input data may comprise patient data, including a 3D image of an area of the patient that is to be treated according to the treatment plan. Instead, or in addition to the images, the input data may comprise an initial treatment plan to be optimized in the optimization step.

If the input data comprise an initial treatment plan, the method may further comprise the step of evaluating the initial plan for the first and the second scenario before selecting first and second goals on which to base the first and second optimization function, respectively.

Traditionally, in scenario-based optimization methods, one set of optimization functions is used for the optimization of all scenarios. This means that the method will try to achieve the same level of goal fulfilment for all scenarios, including the worst-case scenario. If a worst-case based optimization method is used, this means that the quality of the plan will be limited by the most difficult scenario, that is, the scenario that will yield the lowest possible quality plan. In other methods, resources will be used in a less than optimal way, trying to optimize poor scenarios instead of optimizing scenarios that have a greater chance of achieving a satisfactory result. By allowing different optimization functions to be used for each of the different scenarios according to the invention, each scenario can be optimized as much as possible, regardless of the limitations associated with other scenarios. In this way, all scenarios, including the most difficult ones, can be taken into account without limiting the plan quality for the more favourable scenarios. The possibility to consider even poor performance scenarios while still achieving the best possible result for the better scenarios means a significant improvement of the overall plan.

The method according to the invention is particularly useful in cases where information about the achievable level of goal fulfilment in different scenarios is available.

Different scenarios typically include different values for variables such as
- Patient weight, which may remain constant but which in many cases is reduced during a treatment period
- Tumour shrinkage
- Position of patient
- Treatment parameters such as radiobiological model parameters Different goals for different scenarios may imply, for example, that if the tumour remains large a large portion of the tumour must be covered in the radiotherapy, whereas if the tumour shrinks a smaller portion of the tumour needs to be covered. Or that if the tumour is close to an organ at risk a lower dose to the tumour may be accepted to guarantee a lower dose to the organ at risk.

The inventive optimization method may be used advantageously in a number of different types of situations.

For example, in a typical radiotherapy situation, there is a target that should receive at least a minimum dose and an organ at risk that should receive no more than a lower maximum dose. The actual distance between the target and the organ at risk during treatment is unknown due to the uncertainties described above, and therefore a number of different scenarios is defined. In some scenarios the distance between the target and the organ at risk will be big enough to allow a high coverage of the target. In other scenarios the distance between the target and the organ at risk is smaller and it may be necessary to accept some loss of coverage of the target to protect the organ at risk. Using the scenario specific optimization functions according to the invention, the best possible objective function constituents and constraints for each of these scenarios can be achieved without being restricted by the other scenarios.

Scenario-dependent optimization may also be used together with prioritized, or lexicographic, optimization. Prioritized optimization is a semi-automated technique where treatment plans are generated based on a user-specified list of prioritized goals. The plan is optimized to achieve the goals as well as possible in consecutive order according to their priority, starting with the most important goals in the first optimization and using the level of goal achievement attained in one iteration as a constraint during subsequent optimization iterations. According to embodiments of the invention, the constraints related to the previously optimized goals are determined independently per scenario, with the required level of goal achievement in a given scenario set on the basis of the previously observed level of goal achievement in the scenario after the previous optimization. The achievement of each goal, or group of goals within a common priority level, is thus optimized to the extent that it does not interfere with the higher priority goals. According to embodiments of the invention, the constraints related to the previously optimized goals are enforced independently for each scenario in such a way that the required level of goal achievement in one scenario is set on the basis of the previously observed level of goal achievement in that scenario.

For the purpose of prioritized optimization the method may comprise the steps of setting at least a first additional goal for the first or second scenario, said first additional goal being less important than the first goal, the method further comprising the step after the optimization of the radiotherapy treatment plan according to step c. of adding at least one constraint based on the optimized plan to the optimization problem to create an updated first optimization problem, and then performing steps a-c again on the basis of the updated first optimization problem and the first additional goal, thereby obtaining a second optimized radiotherapy treatment plan.

The step of creating the updated first optimization problem preferably comprises omitting the first goal from the objective function, and adding the first additional goal to the objective function, and adding a constraint related to how well the first goal was met according to the first optimized radiotherapy treatment plan.

According to embodiments of the invention the optimization may be used for the purpose of dose mimicking, for example in converting the initial plan to suit another type of radiation or another beam configuration. The common denominator in dose mimicking methods is that optimization is performed with the objective to minimize the discrepancy between the current dose and a reference dose (or between a current dose-volume histogram and a reference dose-volume histogram). Dose mimicking can be used for different types of plan conversion, including the following:
- Conversion from one treatment machine to another, or from one beam configuration to another
- Conversion of an idealized dose into a treatment plan that complies with the physical limitations of the delivery method
- Optimization subject to constraints that prevent some type of dose deterioration, for example, minimization of integral dose while maintaining target coverage and homogeneity.
- Conversion of photon therapy plans to proton therapy plans. In proton therapy planning, uncertainties must be considered, whereas in photon therapy planning it is generally sufficient to apply a margin around the target. If the photon plan was generated using geometric margins, scenario doses for the photon plan can be extracted using the static dose cloud approximation because margins implicitly assume the static dose cloud approximation. This means that the errors are assumed to move the patient or anatomical structures rigidly within a dose distribution that is unaffected by the error. The proton therapy plan can then be generated by optimization with respect to accurate scenario doses.

It is suggested according to the invention to perform dose mimicking with respect to scenario dependent reference dose distributions. Such optimization permits plan conversions to be performed without any unnecessary loss of robustness against errors.

Another example of dose mimicking may be applied when a linear combination of robust proton therapy plans created by multi-criteria navigation is converted to a robust proton plan that is feasible with respect to a minimum spot weight bound. If one or more spots (that is, partitions of the dose delivered from different angles and/or with different energies) in the linear combination of plans has a lower weight than the minimum weight defined in the treatment system, the plan must be recalculated, for example by dose mimicking using the linear combination of scenario doses over the plans as reference dose for each scenario.

The method according to the invention may also be combined with adaptive treatment. In adaptive treatment a new treatment plan is calculated not only before the first treatment fraction but also at one or more additional times during treatment, based on new images of the patient taken at the additional point in time. A new treatment plan may be calculated before each fraction or, for example, once a week. The new treatment plan may be scenario-based according to embodiments of this invention. Therefore, the number of possible scenarios that have to be taken into account, and/or the variation between them can be reduced, since each plan will only cover a portion of the total treatment, which will limit the magnitude of possible changes. The scenarios to include when plans are recalculated could also be based on the observed changes between previous treatment fractions. When combined with adaptive planning, the method will further comprise the step, performed after delivering at least one treatment fraction, of obtaining updated input data and performing the method based on the updated input data. Typically, one or more fraction images will be obtained to provide information about how the patient has changed during the treatment.

The number of scenarios used in each of the embodiments should be sufficient to provide a representation of each scenario that is likely to occur over the period of treatment or, in the case of adaptive treatment planning, the period until the next treatment plan is to be calculated. The actual number of scenarios needed will vary depending on the types and magnitudes of the uncertainties, the size of each region of interest and possibly other factors. In cases involving, for example, minor uncertainty regarding density, 2 or 3 scenarios may be sufficient while for more complex situations several thousand scenarios may be required for a satisfactory result.

Aspects of the invention also relate to a computer program product including computer readable code means which when run in a processor will cause the processor to perform the method according to an embodiment of the invention. A non-transitory computer-readable medium encoded with computer-executable instructions which when run in a processor will cause the processor to perform the method.

Aspects of the invention also relate to a computer system for performing dose calculations for radiotherapy treatment planning, the system comprising processing means, said computer system having a program memory having stored therein a computer program product according to the above in such a way that the computer program product, when executed, will control the processing means to perform a method according to an embodiment of the invention.

BRIEF DESCRIPTION OF THE DRAWINGS

The invention will be described in more detail in the following by way of example only and with reference to the appended drawings, in which.

DETAILED DESCRIPTION OF PREFERRED EMBODIMENTS

Figure 1:
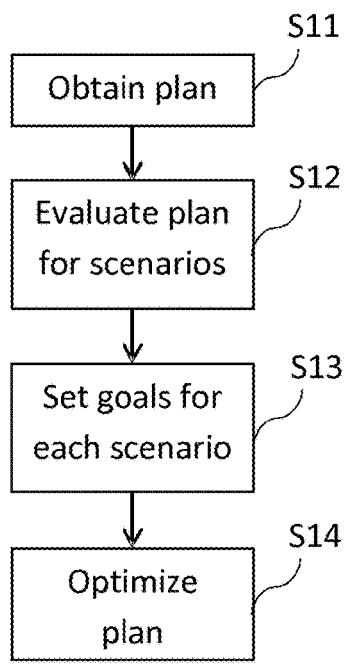
FIG. 1 is a flow chart of an embodiment of the inventive method

FIG. 1 is a flow chart of an embodiment of the method which may be used, for example, in conjunction with dose mimicking. It is also suitable in other types of situations, not involving dose mimicking. In this embodiment the starting point is an initial treatment plan obtained in step S11 and a number of scenarios to consider, and the method aims to obtain an improved treatment plan based on the initial treatment plan, or to obtain a deliverable treatment plan in cases where the initial treatment plan does not satisfy all machine limitations. Depending on the type of data included in the plan, other input data may be needed, for example, data related to the patient, for dose calculation. The initial treatment plan may be obtained in any manner known in the art, including scenario-based and non-scenario-based methods. Typically it will be a previous plan developed for the same patient, but it could also be obtained from a library of standard plans.

The scenarios may be defined manually, or fully automatically. Several semi-automatic ways of defining scenarios are also perceivable. In a preferred embodiment, the user is allowed to set the magnitudes of the uncertainties as input to the system, which will calculate a suitable set of scenarios based on the uncertainties.

In step S12 the initial treatment plan is evaluated for a number of scenarios, with respect to a quality related to at least one aspect of dose to target at different scenarios. The aspect may be related to the dose level, average dose, DVH or the whole dose distribution. As mentioned above, the initial treatment plan is not necessarily obtained using scenario-based methods, but if it is, the scenarios used in step S12 may be different than the ones used for the initial treatment plan. As in all embodiments of the invention, at least two scenarios are used but preferably more, as discussed above. The scenarios are defined with respect to one or more uncertainties, for example regarding one or more of the following:
Setup error
Range error
Organ movement
Patient movement In step S13 different goals are set for each of the scenarios. The goals for each scenario are set to reflect the result that was achieved by the initial plan for that particular scenario. This means that a set of goals for one scenario may be stricter than a corresponding set of goals for an alternative scenario within the same plan. As mentioned above the goals may be set as objective function constituents, as constraints, or a combination of these. Additional goals not reflected by the initial plan could also be included.

In step S14 the new treatment plan is optimized for the new conditions. As explained above, in the case of dose mimicking, this may mean, for example, that the new plan is optimized for a different type of radiation or different beam configuration compared to the initial plan.

Figure 2:
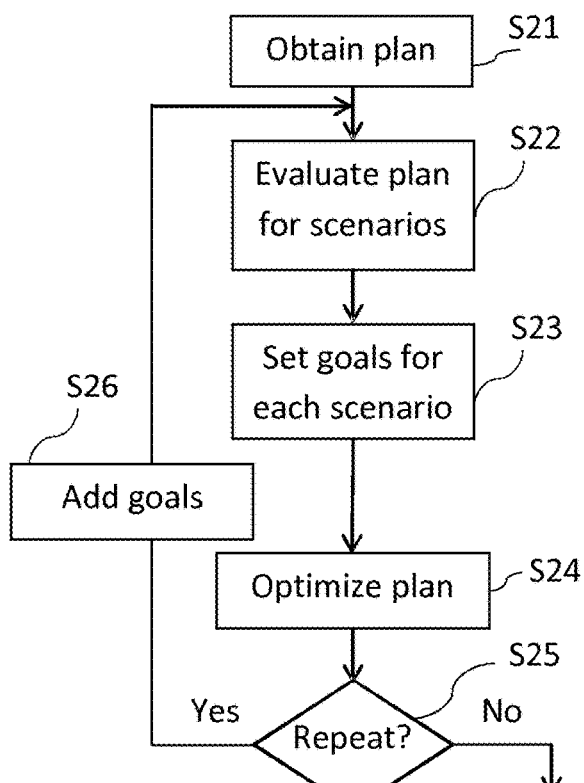
FIG. 2 is a flow chart of an embodiment of the inventive method used in conjunction with prioritized optimization

FIG. 2 is a flow chart of an embodiment of the method when it is used in conjunction with prioritized optimization. In prioritized optimization there are several goals, or sets of goals, having different priorities, and optimization is performed first with respect to the goal or goals having the highest priority. The optimization may then be performed iteratively, for the other goals in decreasing priority order.

Steps S21-S23 are the same as steps S11-S13 in FIG. 1. In step S23 in the first iteration the goal or set of goals having the highest priority is considered. Preferably, optimization functions reflecting these goals are included as objective constituents. In step S24 the plan is optimized based on the goals set in step S23. The plan is then typically evaluated as input data to decision step S25.

If it is determined in step S25 that the plan should be further improved, the level of goal achievement obtained in step S24 is included in the goals for further iterations of the optimization. This is illustrated by step S26, before the method reverts to step S22. Preferably, the goals used in step S23 in the first iteration are discarded and the optimization functions reflecting the goals included in step S26 are included as constraints, typically enforcing consecutive optimizations to achieve at least the level of fulfilment attained in step S24, possibly with a slippage factor to allow for some deviation from the level reached. In the second iteration the goals having the second highest priority will be the goals set in step S23.

In step S25 the decision may be based on the evaluation mentioned above so that if the result of the evaluation is that the quality of the plan is sufficient, the procedure will end. Alternatively the number of iterations of the procedure may be set beforehand, so that the decision will yield a "no" and the procedure will end after a certain number of optimizations of the plan.

In a preferred embodiment of the procedure shown in FIG. 2, step S26 comprises the following amendments to the optimization function: Any objective function constituents relating to at least one goal set for the previous optimization iteration is discarded from the objective function. Instead, preferably, a constraint is added, defined by the degree to which the at least one goal was met in the previous optimization iteration. Typically, the constraint will be that the goal has to be met to at least the same degree in the next optimization, or only deteriorate within a certain limit. For example, if a certain dose coverage of a target is achieved, at least the same dose coverage should be achieved in the next optimization. Also, objective function constituents related to the at least one goal on the next priority level are added to the objective function for the next optimization iteration.

Figure 3:
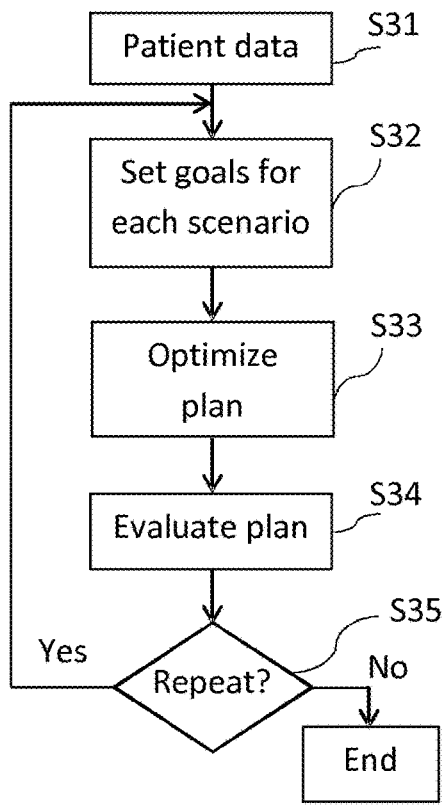
FIG. 3 is a flow chart of an alternative embodiment of the inventive method FIG. 4 discloses schematically a computer system that may be used for performing the invention

FIG. 3 is a flow chart of an embodiment of the method where the procedure starts in step S31 with patient data and a number of different scenarios. The patient data typically includes the planning images of the patient and possibly other data, such as a previous plan, or other geometrical data concerning the patient.

If a plan is included, the plan may be evaluated for different scenarios in a step corresponding step S12, not shown in FIG. 3.

In step S32 different goals are set for the scenarios. This may be performed manually or semi-automatically supported by the system, or automatically. In step S33 the plan is optimized and in step S34 the plan is evaluated. After step S34 a decision step S35 may be performed for determining if further optimization should be carried out. If so, the procedure reverts to step S32, if not, the procedure ends. The decision to end the procedure can depend on many different aspects known in the art, such as for example the size of the improvement relative to the previous step, the time spent by the method, the number of steps taken or that the desired level of quality has been met. If no plan was included in the patient data, the planning system will develop an initial guess as a starting point for optimizing the plan.

Figure 4:
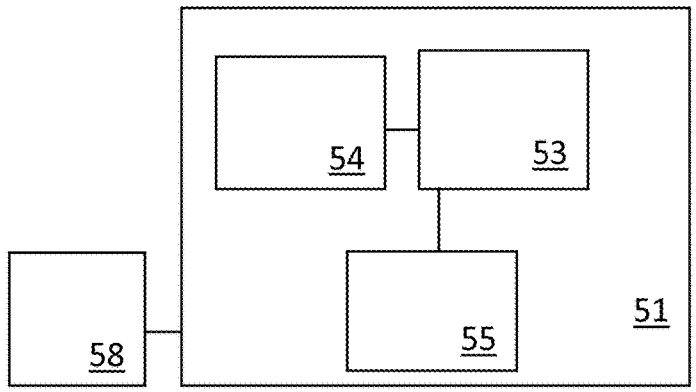

FIG. 4 is a schematic representation of a computer system in which the inventive method may be performed. A computer 51 comprises a processor 53, a data memory 54 and a program memory 55. Preferably, a user input means 58 is also present, in the form of a keyboard, a mouse, a joystick, voice recognition means or any other available user input means.

The data memory holds input data for the method. The type of input data depends on the embodiment. Input data may include a treatment plan, patient data, one or more value sets and one or more objective functions, as well as the scenarios to be considered during optimization. The data in the data memory may be generated in the computer 51, entered by means of the user input means or received from another storage means, in any way known in the art.

As will be understood, the data memory 54 is only shown schematically. There may be several data memory units, each holding one or more different types of data, for example, one data memory for the value set, one for the objective function, etc.

The program memory 55 holds a computer program arranged to control the processor to perform the optimization. It will be understood that not all of the steps of the method of the respective flowcharts of FIGS. 1, 3 and 2 are necessarily performed in the computer 51.

The invention claimed is:

1. A method for radiotherapy treatment plan optimization using a scenario-based optimization function to perform optimization based on at least a first and a second scenario, each scenario representing the realization of at least one uncertainty, the method comprising the steps of:
   a. providing input data for treatment plan optimization;
   b. defining a first optimization function for the first scenario;
   c. defining a second optimization function for the second scenario, said second optimization function being different from the first optimization function, such that different optimization functions are used for the first and second scenario, respectively; and
   d. optimizing a radiotherapy treatment plan applying the first optimization function under the first scenario and the second optimization function under the second scenario, thereby obtaining a first optimized radiotherapy treatment plan.

2. The method according to claim 1, wherein the first optimization function and/or the second optimization function is included as a constraint in the optimization.

3. The method according to claim 1, wherein the first optimization function and/or the second optimization function is included as an objective function constituent in the optimization.

4. The method according to claim 1, wherein the input data comprise patient data, including a 3D image of an area of the patient that is to be treated according to the treatment plan.

5. The method according to claim 1, wherein the input data comprise an initial treatment plan.

6. The method according to claim 5, further comprising the steps of evaluating the initial plan for the first and the second scenario, selecting a first and a second goal based on the evaluations, and basing the first and second optimization functions on the first and second goal, respectively.

7. The method according to claim 5, wherein optimization involves dose mimicking in converting the initial plan to suit another type of radiation or another beam configuration.

8. The method according to claim 1, wherein at least a first additional goal is set for the first or second scenario, said first additional goal being less important than a first goal set in the first optimization, the method further comprising the step after the optimization of the radiotherapy treatment plan according to step d. of adding at least one constraint based on the optimized plan to the optimization problem to create an updated first optimization problem, and then performing steps b-d again on the basis of the updated first optimization problem and the first additional goal, thereby obtaining a second optimized radiotherapy treatment plan.

9. The method according to claim 8, wherein the step of creating the updated first optimization problem comprises omitting the first goal from the objective function, and adding the first additional goal to the objective function, and adding a constraint related to how well the first goal was met according to the first optimized radiotherapy treatment plan.

10. A computer program product comprising a non-transitory computer readable medium encoded with computer-executable instructions which when run in a processor will cause the processor to perform the method according to claim 1.

11. A computer system for performing dose calculations for radiotherapy, the system comprising a processor, said computer system having a program memory having stored therein a computer program product according to claim 10 in such a way that the computer program product, when executed, will control the processor.

* * * * *